United States Patent
Mori et al.

(10) Patent No.: US 9,275,456 B2
(45) Date of Patent: Mar. 1, 2016

(54) IMAGE SEARCH ENGINE

(75) Inventors: Susumu Mori, Ellicott City, MD (US); Michael I. Miller, Baltimore, MD (US); Kenichi Oishi, Lutherville-Timonium, MD (US); Andreia V. Faria, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 245 days.

(21) Appl. No.: 13/824,853

(22) PCT Filed: Oct. 25, 2011

(86) PCT No.: PCT/US2011/057692
§ 371 (c)(1),
(2), (4) Date: May 14, 2013

(87) PCT Pub. No.: WO2012/058217
PCT Pub. Date: May 3, 2012

(65) Prior Publication Data
US 2013/0223716 A1   Aug. 29, 2013

Related U.S. Application Data

(60) Provisional application No. 61/408,249, filed on Oct. 29, 2010.

(51) Int. Cl.
*G06T 7/00* (2006.01)
*A61B 5/00* (2006.01)
(Continued)

(52) U.S. Cl.
CPC ............. *G06T 7/0014* (2013.01); *A61B 5/0013* (2013.01); *A61B 5/055* (2013.01);
(Continued)

(58) Field of Classification Search
None
See application file for complete search history.

(56) References Cited

U.S. PATENT DOCUMENTS 5,905,819 A * 5/1999 Daly ..................... G06T 1/0028
358/1.9
8,805,013 B2 * 8/2014 Amemiya ............ G06K 9/6203
382/103

(Continued)

OTHER PUBLICATIONS

Trachet et al. "Resolving In-Vivo Flow Fields in the Systemic Circulation of the Mouse through Combined Ultrasound Imaging and Computational Fluid Dynamics" IEEE (2010) pp. 1-4.*

(Continued)

*Primary Examiner* — Stephen R Koziol
*Assistant Examiner* — Mia M Thomas
(74) *Attorney, Agent, or Firm* — Venable LLP; Henry J. Daley; Trent B. Ostler

(57) ABSTRACT

An embodiment of the current invention includes a non-invasive imaging system, comprising: an imaging scanner suitable to generate an image representing a tissue region of a subject under observation, the tissue region having at least one substructure and the image comprising a plurality of image voxels; a signal processing system in communication with the imaging scanner to receive the imaging signal from the imaging scanner; and a data storage unit in communication with the signal processing system, wherein the data storage unit is configured to store: an atlas comprising spatial information of the at least one substructure in the tissue region, and a database comprising a plurality of pre-stored medical images representing the tissue region, and wherein the signal processing system is adapted to: identify, based on the atlas and for each of the at least one substructure, a corresponding portion of image voxels in the image; provide a computed quantification of the corresponding portion of image voxels for each of the at least one substructure of the tissue region by performing spatial filtering on the image; and search the database to provide at least one selected medical image from the plurality of pre-stored medical images, the at least one selected medical image having a corresponding quantification that is substantially similar to the computed quantification.

29 Claims, 8 Drawing Sheets

(51) Int. Cl.
*A61B 5/055* (2006.01)
*G06F 17/30* (2006.01)
*G06F 19/00* (2011.01)
*A61B 6/03* (2006.01)
*A61B 6/00* (2006.01)
*A61B 8/00* (2006.01)

(52) U.S. Cl.
CPC ........ *G06F17/30247* (2013.01); *G06F 19/321* (2013.01); *G06F 19/3443* (2013.01); *A61B 6/032* (2013.01); *A61B 6/501* (2013.01); *A61B 6/56* (2013.01); *A61B 8/56* (2013.01); *A61B 8/565* (2013.01)

(56) References Cited

U.S. PATENT DOCUMENTS

| | | | |
|---|---|---|---|
| 2003/0013951 A1* | 1/2003 | Stefanescu et al. | 600/407 |
| 2005/0010445 A1* | 1/2005 | Krishnan et al. | 705/2 |
| 2005/0190984 A1* | 9/2005 | Fischer | G06T 11/008 382/260 |
| 2006/0069318 A1* | 3/2006 | Keaveny et al. | 600/300 |
| 2006/0251304 A1* | 11/2006 | Florin | G06T 7/0083 382/128 |
| 2006/0269130 A1* | 11/2006 | Maroy | G06T 7/0081 382/173 |
| 2006/0277073 A1* | 12/2006 | Heilbrunn et al. | 705/2 |
| 2007/0147674 A1* | 6/2007 | Gundel | G06T 5/20 382/131 |
| 2007/0165920 A1* | 7/2007 | Gering | A61B 5/055 382/128 |
| 2007/0223799 A1* | 9/2007 | Weiss | 382/131 |
| 2007/0248254 A1* | 10/2007 | Mysore Siddu et al. | 382/131 |
| 2008/0075348 A1* | 3/2008 | Rappaport et al. | 382/132 |
| 2009/0006131 A1* | 1/2009 | Unger et al. | 705/3 |
| 2009/0041322 A1* | 2/2009 | Wolf | 382/131 |
| 2009/0074272 A1* | 3/2009 | Lu et al. | 382/128 |
| 2009/0129642 A1* | 5/2009 | Matsumoto | 382/128 |
| 2009/0297012 A1* | 12/2009 | Brett et al. | 382/132 |
| 2010/0111386 A1* | 5/2010 | El-Baz | G06T 7/0016 382/128 |
| 2010/0201687 A1* | 8/2010 | Breeuwer | G06T 15/08 345/424 |
| 2010/0250275 A1* | 9/2010 | Sakagawa et al. | 705/2 |
| 2010/0293164 A1* | 11/2010 | Weese et al. | 707/737 |
| 2010/0316277 A1* | 12/2010 | Fan | G06T 7/0028 382/131 |
| 2011/0121163 A1* | 5/2011 | Kang et al. | 250/252.1 |
| 2012/0013779 A1* | 1/2012 | Hattery | A61B 5/0059 348/302 |
| 2012/0143090 A1* | 6/2012 | Hay et al. | 600/587 |
| 2012/0148123 A1* | 6/2012 | Gindele | 382/128 |
| 2012/0157851 A1* | 6/2012 | Zwirn | A61B 8/4488 600/447 |
| 2013/0034278 A1* | 2/2013 | Gindele et al. | 382/128 |
| 2013/0102877 A1* | 4/2013 | Mori | A61B 5/055 600/410 |

OTHER PUBLICATIONS

Valdes, M et al. "Atlas-Based Segmentation and Tracking of 3D Cardiac MR Images Using Non-rigid Registration" T. Dohi and R. Kikinis (Eds.): MICCAI 2002, LNCS 2488, pp. 642-650, 2002. _c Springer-Verlag Berlin Heidelberg 2002.*

Granander and Miller, 1996, Statistical computing and graphics newsletter 7, 3-8.

Joshi et al., "On the differential geometry of the Cortical surface," 1995, Geometric methods in Applied Imaging, San Diego, CA, 2573, 304-311.

Miller et al., "Mathematical textbook of deformable neuroanatomies," 1993, Proc Natl Acad Sci, 90, 11194-11948.

* cited by examiner

IMAGE SEARCH ENGINE

CROSS-REFERENCE OF RELATED APPLICATION

This application claims priority to U.S. Provisional Application No. 61/408,249 filed on Oct. 29, 2010, the entire contents of which are hereby incorporated by reference, and is a U.S. national stage application under 35 U.S.C. §371 of PCT/US2011/057692, filed Oct. 25, 2011, the entire contents of which are incorporated herein by reference.

BACKGROUND

1. Field of Invention

The current invention relates to non-invasive imaging systems and methods, and more particularly to imaging systems and methods that provide computer assisted diagnosis of tissue abnormalities in human and animal subjects.

2. Discussion of Related Art

Google does word searches through the internet, but it can't search if provided with a picture and asked to find a similar picture. The absence of this search capability hinders the utilization of modern medical images that are stored in a clinical database. In particular, although the clinical database may be extremely rich, it has been rarely used to enrich current diagnosis. This discrepancy is largely due to the lack of a search engine that can extract past similar cases. Therefore, there is a need in the art for an image search engine.

SUMMARY

An embodiment of the current invention includes a non-invasive imaging system, comprising: an imaging scanner suitable to generate an image representing a tissue region of a subject under observation, the tissue region having at least one substructure and the image comprising a plurality of image voxels; a signal processing system in communication with the imaging scanner to receive the imaging signal from the imaging scanner; and a data storage unit in communication with the signal processing system, wherein the data storage unit is configured to store: an atlas comprising spatial information of the at least one substructure in the tissue region, and a database comprising a plurality of pre-stored medical images representing the tissue region, and wherein the signal processing system is adapted to: identify, based on the atlas and for each of the at least one substructure, a corresponding portion of image voxels in the image; provide a computed quantification of the corresponding portion of image voxels for each of the at least one substructure of the tissue region by performing spatial filtering on the image; and search the database to provide at least one selected medical image from the plurality of pre-stored medical images, the at least one selected medical image having a corresponding quantification that is substantially similar to the computed quantification.

Another embodiment of the current invention provides a workstation, comprising a receiving engine adapted to: receive an input medical image representing a tissue region from a subject, the input medical image comprising a plurality of image voxels; receiving an atlas of the tissue region, the atlas comprising spatial information of at least one substructure in the tissue region; and receiving a database comprising a plurality of pre-stored medical images representing the tissue region; a computing engine adapted to: identify, for each of the at least one substructure in the tissue region, a corresponding portion of image voxels in the input medical image by using the spatial information from the atlas; provide, for each of the at least one substructure in the tissue region, a computed quantification of the corresponding portion of image voxels by performing spatial filtering on the input medical image; a search engine adapted to search the database to select at least one of the plurality of pre-stored medical images with a corresponding quantification that is substantially similar to the computed quantification.

Yet another embodiment of the current invention provides a computer readable medium comprising software instructions, which instructions when executed by a computer, causes the computer to: receive, from a first data storage device, an input medical image representing a tissue region from a subject, the input medical image comprising a plurality of image voxels; receive, from the first data storage device or a second data storage device, a atlas of the tissue region, the atlas comprising spatial information of at least one substructure in the tissue region; receive, from the first data storage device or the second data storage device or a third data storage device, a medical image database comprising a plurality of pre-stored medical images; identify, for each of the at least one substructure of the tissue region, a corresponding portion of image voxels in the input medical image by using the spatial information in the atlas; provide, for each of the at least one substructure of the tissue region, a computed quantification of the corresponding portion of image voxels by performing spatial filtering on the input medical image; search the database to select at least one of the plurality of pre-stored medical images having a corresponding quantification that is substantially similar to the computed quantification.

Still another embodiment of the current invention provides a computer-implemented method to construct a medical image database, the method comprising: receiving, from a first data storage device, a medical image representing a tissue region of a subject, the medical image comprising a plurality of image voxels; receiving, from the first or a second data storage device, an atlas of the tissue region, the atlas comprising spatial information of at least one substructure of the tissue region; identifying, on the medical image, image voxels corresponding to each of the at least one substructure of the tissue region; performing spatial filtering on the medical image based on the image voxels identified for each of the at least one substructure to provide a computed quantification thereof; and storing, in the database, information encoding the computed quantification for each of the at least one substructure identified on the medical image in the database, the database residing on the first or the second data storage device or a third data storage device.

One more embodiment of the current invention provides a workstation, comprising: a receiving engine adapted to: receive a medical image representing a tissue region from a subject, the medical image comprising a plurality of image voxels; and receive an atlas of the tissue region, the atlas comprising spatial information encoding at least one substructure of the tissue region; and a computing engine adapted to: identify, according to spatial information in the atalas, image voxels from the medical image that correspond to each of the at least one substructure of the tissue region; perform spatial filtering on the medical image based on the image voxels identified for each of the at least one substructure to provide a computed quantification thereof; and store, on a data storage device, information encoding the computed quantification of each of the at least one substructure identified on the medical image, wherein the information provides an addition to a database of medical images residing on the data storage device.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing the embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
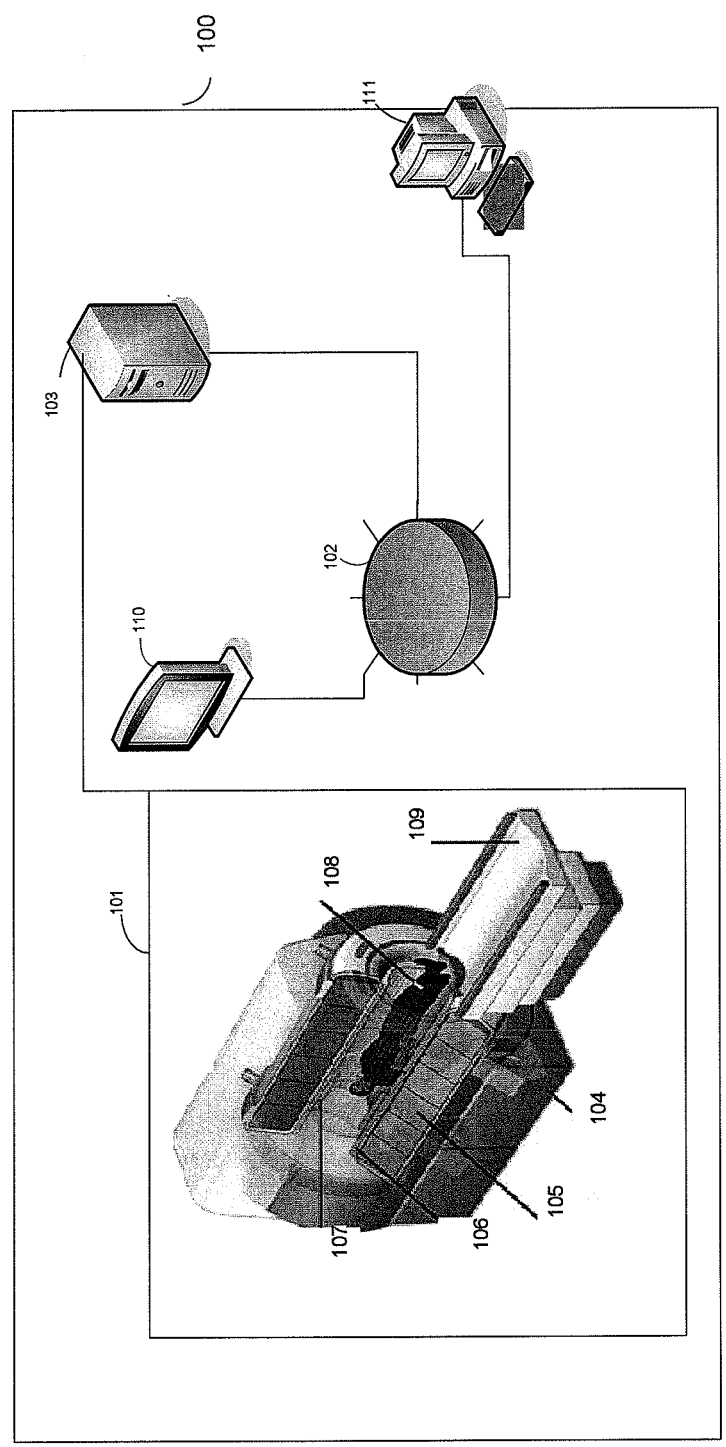
FIG. 1 is a schematic illustration of a non-invasive imaging system according to an embodiment of the current invention.

FIG. 1 is a schematic illustration of a non-invasive imaging system 100 according to some embodiments of the current invention. The non-invasive imaging system 100 includes an imaging scanner 101, a data storage unit 102, and a signal processing system 103. Imaging scanner 101 may be, but is not limited to, a magnetic resonance imaging (MRI) scanner, a computed tomography (CT) scanner, a positron emission tomography (PET) scanner, a single positron emission computed tomography (SPECT) scanner, an ultrasound scanner, an optical coherence tomography (OCT) scanner, or a microscope. For example, an MRI scanner may have a base 104 to support a main magnet 105 (providing a substantially uniform main magnetic field $B_0$ for a subject 108 under observation on scanner bed 109), a gradient system 106 (providing a perturbation of the main magnetic field $B_0$ to encode spatial information of the constituent water molecules of subject 108 under observation), and a radio-frequency (RF) coil system 107 (transmitting electromagnetic waves and receiving magnetic resonance signals from subject 108).

Data storage unit 102 may store atlas data corresponding to a tissue region of subject 108 under observation. The tissue region may be, for example, a brain, a heart, a liver, a muscle, a kidney, a breast, a joint, a vessel, or other intended organ of subject 108. The term "atlas" used herein does not necessarily require an actual material object, such as a three dimensional material object. It will be used generally to also refer to data or information that represents a spatial and geometrical configuration.

For example, data storage unit 102 may store an atlas of the tissue region including spatial information of the anatomical substructures of the tissue region. For example, the atlas may represent a human brain and may include information encoding location and shape of the various cortical substructures, etc. The atlas can be constructed to take into account variations between genders, races, or other subpopulations based on the potential application.

The atlas of the tissue region may also include, for example, spatial information of physiological substructures of the tissue region. For example, a brain tissue may have the physiological substructures of the gray matter, the white matter, and the cerebrospinal fluid (CSF).

The images used to construct the atlas, may include, for example, MRI images, CT images, PET images, SPECT images, ultrasound images, OCT image, microscopy images etc. The atlas may incorporate information from images from at least one subject that is different from subject 108 under observation. The atlas may incorporate information from images from a previous scan of subject 108 under observation. The atlas may be derived from images of a variety of different contrasts, each favorably delineating, for example, certain substructures in the tissue region. For example, $T_1$-weighted magnetic resonance images suitable for the cortex and deep gray matter of the brain may be used. For example, $T_2$-weighted magnetic resonance images having higher contrasts for the ventricles of the brain may be used. For example, diffusion tensor images in which intra-white matter structures of the brain are best delineated may be used.

The atlas may include spatial information, such as, for example, shape information, location information, of the tissue region. The atlas may further incorporate variability information associated with registering the spatial information to the soft tissue region in the images from a subpopulation of the subject. Registering the spatial information of an atlas to the soft tissue region in an image from a subject may involve warping or transforming (e.g., translation, scaling, deforming, etc.) the geometric information of the atlas to align with the soft tissue region in the image. Registering may also be referred to as normalizing.

The term "atlas" includes, but is not limited to the above examples.

Additionally, data storage unit 102 may store a database that includes a plurality of medical images representing the tissue region of subject 108 under observation. The database may comply with a Digital Imaging and Communications in Medicine (DICOM) standard. The database may be further integrated into a Picture Archiving and Communication System (PACS). The pre-stored medical images may be 3-dimensional (3-D) images.

Data storage unit 102 may be, for example, a hard disk drive, a network area storage (NAS) device, a redundant array of independent disks (RAID), a flash drive, an optical disk, a magnetic tape, a magneto-optical disk, etc. However, the data storage unit 102 is not limited to these particular examples. It can include other existing or future developed data storage devices without departing from the scope of the current invention.

Signal processing system 103 is in communication with imaging scanner 101 to receive an image generated by imaging scanner 101 representing a tissue region of subject 108 under observation. Signal processing system 103 may be partially or totally incorporated within a structure housing imaging scanner 101. Signal processing system 103 may be at least partially incorporated in a workstation that is structurally separate from and in communication with imaging scanner 101. Signal processing system 103 may be incorporated in a workstation that is structurally separate from and in communication with imaging scanner 101. The image may be, for example a magnetic resonance imaging (MRI) image associated with a magnetic resonance contrast parameter, such as, for example, a relaxation time $T_1$, a relaxation time $T_2$, an apparent diffusion coefficient, a property associated with the blood oxygenation level dependent (BOLD) effect, a property associated with the diffusion tensor, etc.

Signal processing system 103 is in communication with data storage unit 102. Signal processing system 103 is adapted to: identify, based on the atlas and for each of the at least one substructure in the image, a corresponding portion of image voxels in the image; provide a computed quantification of the corresponding portion of image voxels for each of the at least one substructure of the tissue region by performing spatial filtering on the image; and search the database to provide at least one selected medical image from the plurality of pre-stored medical images in the database, the at least one selected medical image having a corresponding quantification that is substantially similar to the computed quantification.

Signal process system 103 may be further adapted to display at least one of the image representing the tissue region of subject 108 under observation, or the at least one selected medical image from the plurality of pre-stored medical images on a viewing station 110 or a console station 111. Viewing station 110 or a console station 111 may be, for example, a display device or a printing device. Example display devices may include, for example, a cathode ray tube (CRT), a light-emitting diode (LED) display, a liquid crystal display (LCD), a digital light projection (DLP) monitor, a vacuum florescent display (VFDs), a surface-conduction electron-emitter display (SED), a field emission display (FEDs), a liquid crystal on silicon (LCOS) display, etc. Example printing devices may include, for example, toner-based printers, liquid ink-jet printers, solid ink printers, dye-sublimation printers, and inkless printers such as thermal printers and ultraviolet (UV) printers, etc. However, display and printing devices are not limited to these particular examples. They can Include other existing or future developed devices without departing from the scope of the current invention.

Figure 2:
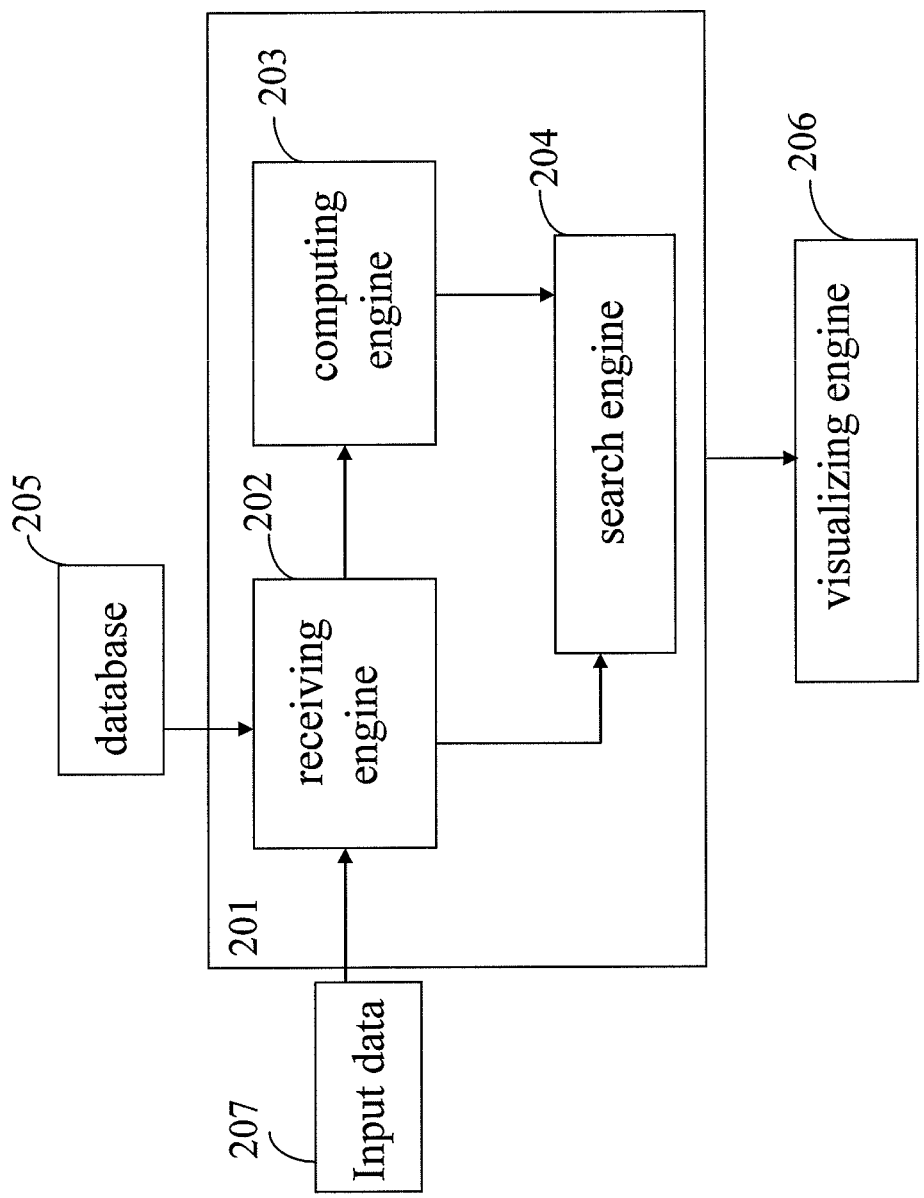
FIG. 2 shows the schematic of a workstation according to some embodiments of the current invention.

FIG. 2 shows the schematic of a workstation 201 according to some embodiments of the current invention. The workstation 201 may include a receiving engine 202, computing engine 203, search engine 204. Receiving engine 202 may be adapted to receive an input medical image representing a tissue region from a subject, the input medical image is a digital image and includes a plurality of image voxels. The subject may be a human patient, an animal, or a sample. Receiving engine 202 may also receive an atlas of said tissue region. The atlas may include spatial information of at least one substructure in the tissue region. The input medical image and the atlas may be represented as input data 207. Receive engine 202 may additionally receive a database 205 comprising a plurality of medical images representing the tissue region. Database 205 may be pre-stored on data storage device 102. Database 205 may comply with a Digital Imaging and Communications in Medicine (DICOM) standard. Database 205 may be further integrated into a Picture Archiving and Communication System (PACS).

Computing engine 203 may be adapted to identify, for each of the at least one substructure in the tissue region, a corresponding portion of image voxels in the input medical image based on the spatial information from the atlas; and provide, for each of the at least one substructure in the tissue region, a computed quantification of the corresponding portion of image voxels by performing spatial filtering on the input medical image. The identified structure could be as small as one voxel or a group of voxels.

Search engine 204 may be adapted to search the database to select at least one of the plurality of pre-stored medical images with a corresponding quantification that is substantially similar to the computed quantification provided by computing engine 203. Search engine 204 may be further adapted to provide a statistical report for the subject. The statistic report is based on said search and may include at least one of: a diagnosis, a prognosis, or functional status.

Workstation 201 may further comprise visualization engine 206 adapted to display the at least one of the medical images selected by search engine 204. Visualization engine 205 may be, for example, a display device or a printing device. Example display devices may include, for example, a cathode ray tube (CRT), a light-emitting diode (LED) display, a liquid crystal display (LCD), a digital light projection (DLP) monitor, a vacuum florescent display (VFDs), a surface-conduction electron-emitter display (SED), a field emission display (FEDs), a liquid crystal on silicon (LCOS) display, etc. Example printing devices may include, for example, toner-based printers, liquid ink-jet printers, solid ink printers, dye-sublimation printers, and inkless printers such as thermal printers and ultraviolet (UV) printers, etc. However, display and printing devices are not limited to these particular examples. They can include other existing or future developed devices without departing from the scope of the current invention.

Figure 3:
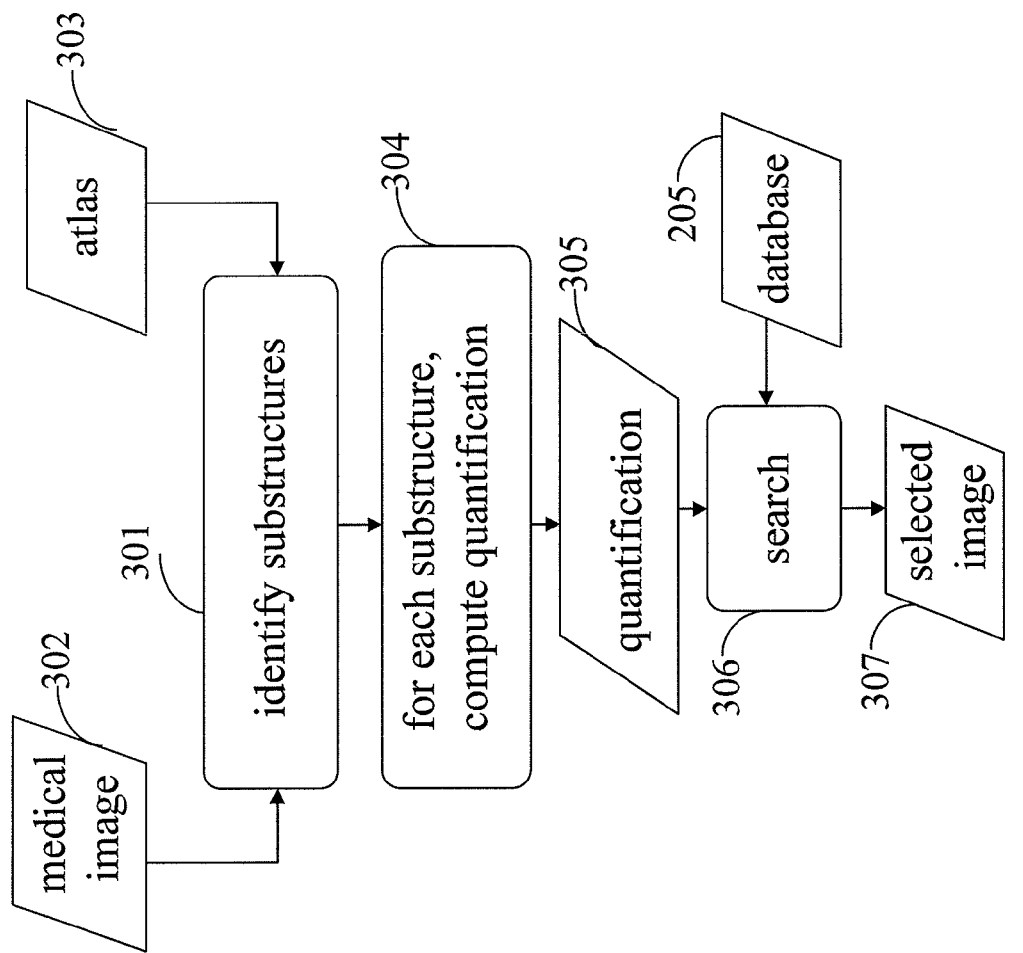
FIG. 3 shows a flow chart according to some embodiments of the current invention.

FIG. 3 shows a flow chart according to some embodiments of the current invention. In particular, these embodiments comprise computer-readable medium containing software instructions, which software instructions when executed by a computer, causes the computer to execute the flow chart according to FIG. 3. Example computer-readable medium may include a Compact Disc-Read-Only Memory (CD-ROM), a Digital Versatile Disk (DVD), a Blue-Ray disc, a flash drive, a floppy disk, a magnetic tape, etc. A computer-readable medium is not limited to these examples and may include other existing or future developed non-transitory medium without departing from the scope of the current invention.

In block 301, an input medical image 302 representing a tissue region of a subject may be received from a first data storage device. The input medical image may include a plurality of image voxels. Input medical image 302 may include a 3-D image.

Figure 4:
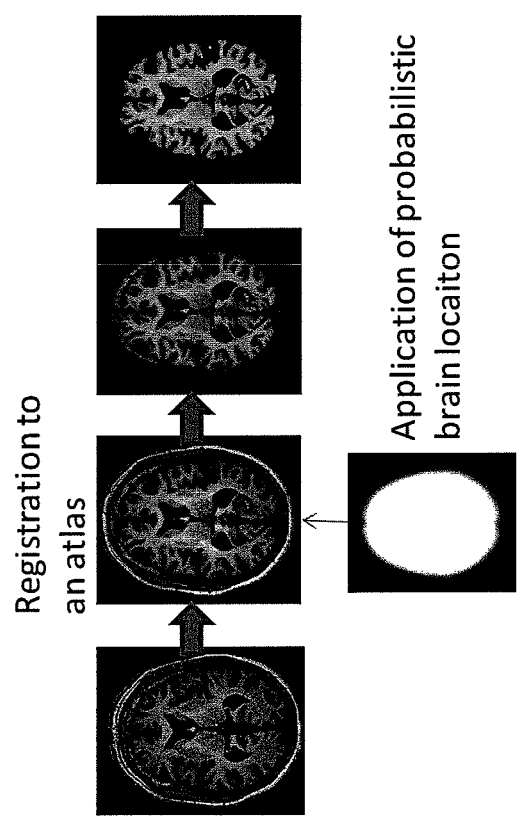
FIG. 4 illustrates an example tissue extraction according to some embodiments of the current invention.

FIG. 4 illustrates an example tissue extraction according to some embodiments of the current invention. Input medical image 302 of a tissue region may be pre-processed such that data representing the organ of interest is extracted from data encoding the surrounding structures. For example, FIG. 4 shows an example brain extracted from the skull in the medical image for subsequent processing. The extracted structure could be the entire brain, a portion of the brain, or other organs.

In block 301 of FIG. 3, an atlas 303 of said tissue region may be received, from the first data storage device or a second data storage device. The atlas may comprise spatial information of at least one substructure in the tissue region. The substructure could be a group of voxels or as small as one voxel.

In block 304 of FIG. 3, a portion of image voxels corresponding to each of the at least one substructure of said tissue region may be identified on input medical image 302. The identification may utilize the spatial information of the at least one substructure in the atlas 303.

Figure 5:
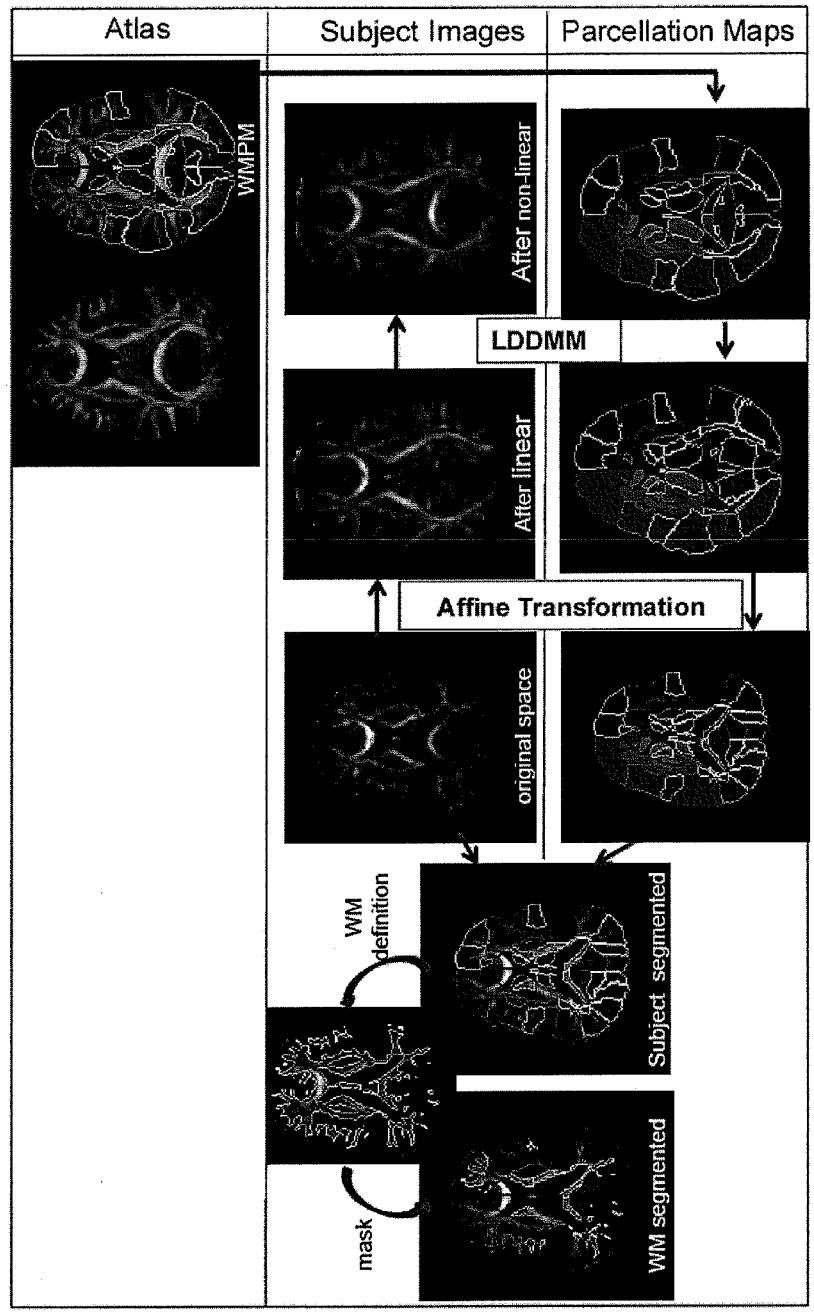
FIG. 5 shows an example of the identification of substructures within the tissue region according to some embodiments of the current invention.

FIG. 5 shows an example of the identification of substructures within the tissue region according to some embodiments of the current invention. According to FIG. 5, brain image of a subject may be registered to an atlas via a transformation to identify the anatomical substructures in the gray matter and white matter regions. This identification may also be known as segmentation in the art. The transformation may be an elastic transformation that preserves the topology of the substructures shown in the input medical image 302. An example elastic transformation may include the Large Deformation Diffeomorphic Metric Mapping (LDDMM) (Miller et al., 1993, Proc Natl Acad Sci, 90, 1194-11948; Joshi et al., 1995, Geometric methods in Applied Imaging, San Diego, Calif.; Granander and Miller, 1996, Statistical computing and graphics newsletter 7, 3-8) and other types of diffeomorphic transformation methods. There can be several important technically attractive features of diffeomorphic transformation (DT). First, DT is highly non-linear and can match the shapes of two brains. It can even transform a brain with severe atrophy. Second, DT can achieve topology preservation. Topology preservation may be a very important feature when applying a morphing algorithm to a biological entity. For example, when morphing one face to another, if topology is not preserved, non-biological results can occur (e.g., two eyes become three eyes). Third the transformation can be reciprocal. Other transformation algorithms that can generate image transformation and preserve tissue topology can be used instead of DT. In some cases, e.g. when only subtle changes in soft tissue regions are expected, the requirement of topology preserving can be waived.

Based on the portion of image voxels identified in block 304 of FIG. 3, a computed quantification 305 of the portion of image voxels corresponding to each of the at least one substructure of said tissue region may be provided by performing spatial filtering on said medical image. Computed quantification 305 may include, for example, a volume, an area, a sum, a mean, a median, a standard deviation, a standard error, etc.

In block 306 of FIG. 3, database 205 may be searched to select at least one of the plurality of pre-stored medical images with a corresponding quantification that is substantially similar to the computed quantification 305. The search may include at least one correlation analysis. The correlation analysis may further include one of: a principal component analysis (PCA), a maximum likelihood analysis, a least mean square analysis, or a student t-test.

Figure 6:
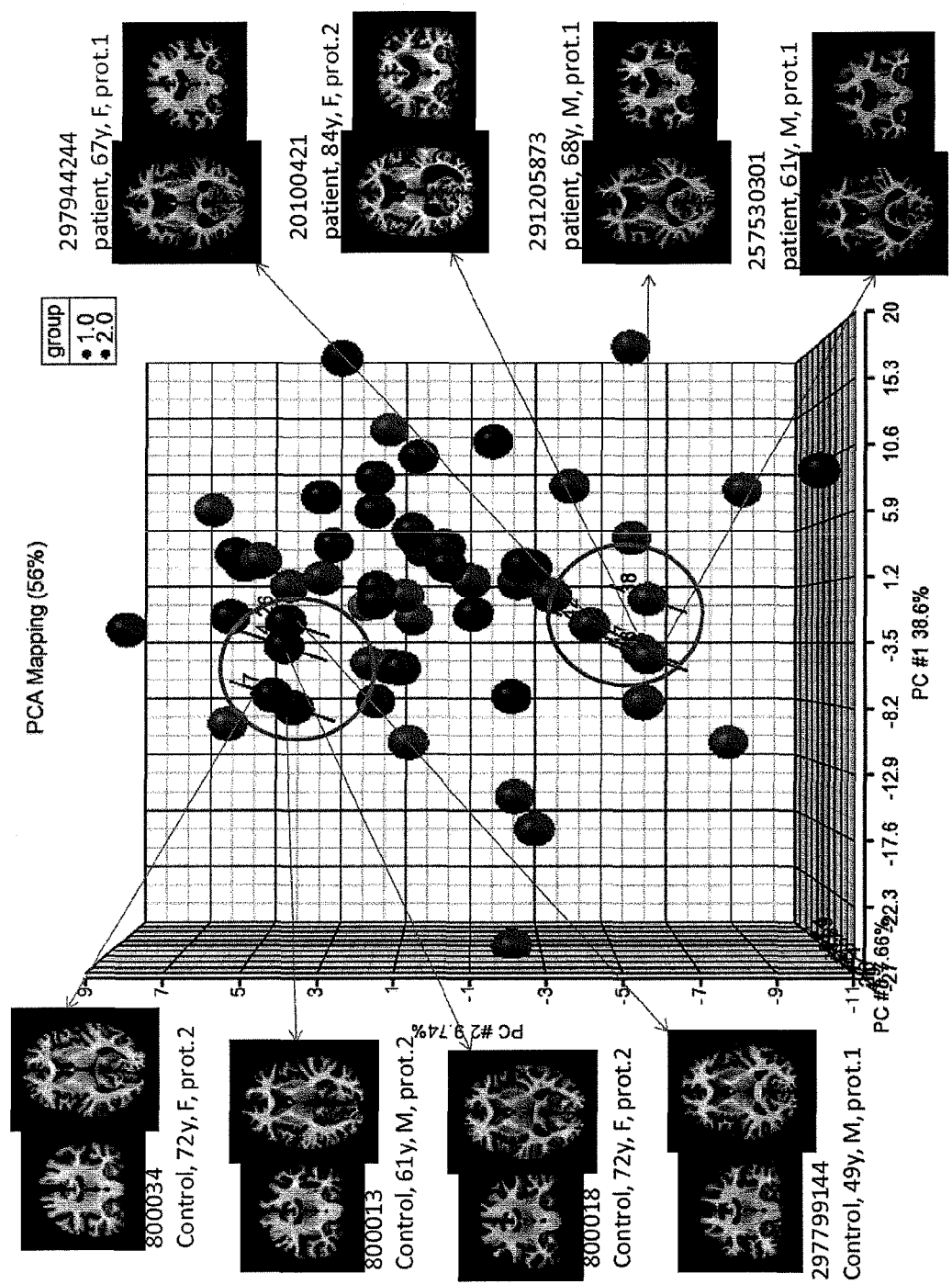
FIG. 6 shows the result from an example correlation analysis for two groups of subjects.

FIG. 6 shows the result from an example correlation analysis for two groups of subjects. An image pool that includes images from both patients and normal control subjects, as identified per conventional behavioral tests, was used in FIG. 6. The images were registered to a brain atlas to identify a total of more than 200 substructures. The volumes of these substructures for each image were calculated so that each image was reduced to the abstraction of a vector. Thereafter, the vectors from the image pool underwent a PCA analysis, in which the two data points closest in the given space are deemed to have similar anatomical features. FIG. 6 demonstrates a sufficient differentiation of the two groups, namely, patient and normal control, as a proof of feasibility for the proposed search engine.

In general, this identification of block 304 can be performed by any two images using a transformation algorithm. For example, given an input image of the brain and N images inside a database, N matchings may be performed between the input image of the brain and each image inside the database. N transformation matrices may thus be obtained. The N transformation matrices may be analyzed to, for example, find the one image inside the database with least transformation. In this approach, each voxel can be considered as measured structures. This is a valid approach. However, a problem of this approach is that, with more accurate and high-dimensional transformation, the amount of information and computational time become too large. It becomes prohibitively difficult to search the same shape from a vast database using this approach.

In another example, the input brain image and the N images inside the database may be transformed based on a brain atlas. Under this approach, N+1 transformation matrices may be obtained between the N+1 images and the atlas. Under this approach, an extra subsequent step may enhance the search efficiency. Namely, after the atlas has been applied to the images to segment the substructures, the properties of the segmented substructures can be recorded. For example, the N images in the database may be segmented into 200 substructures according to the brain atlas having the spatial information of the 200 substructures and the volume of the each substructure may be recorded in the database 205 for each image. Consequently, each brain image in the database may be converted to a vector with 200 elements. This vector abstraction of the image can be stored in the database, together with the each of the N images. Once the images are converted to a vector or a matrix, many simple correlation analyses can be performed to find another vector/matrix that shares the similar feature. Thus, when a new image becomes available, the new image may also be converted to a 200-element vector. Then the searching for an image with similar anatomical feature can be performed by finding another 200-element vector with the highest correlation among the N data.

Figure 7:
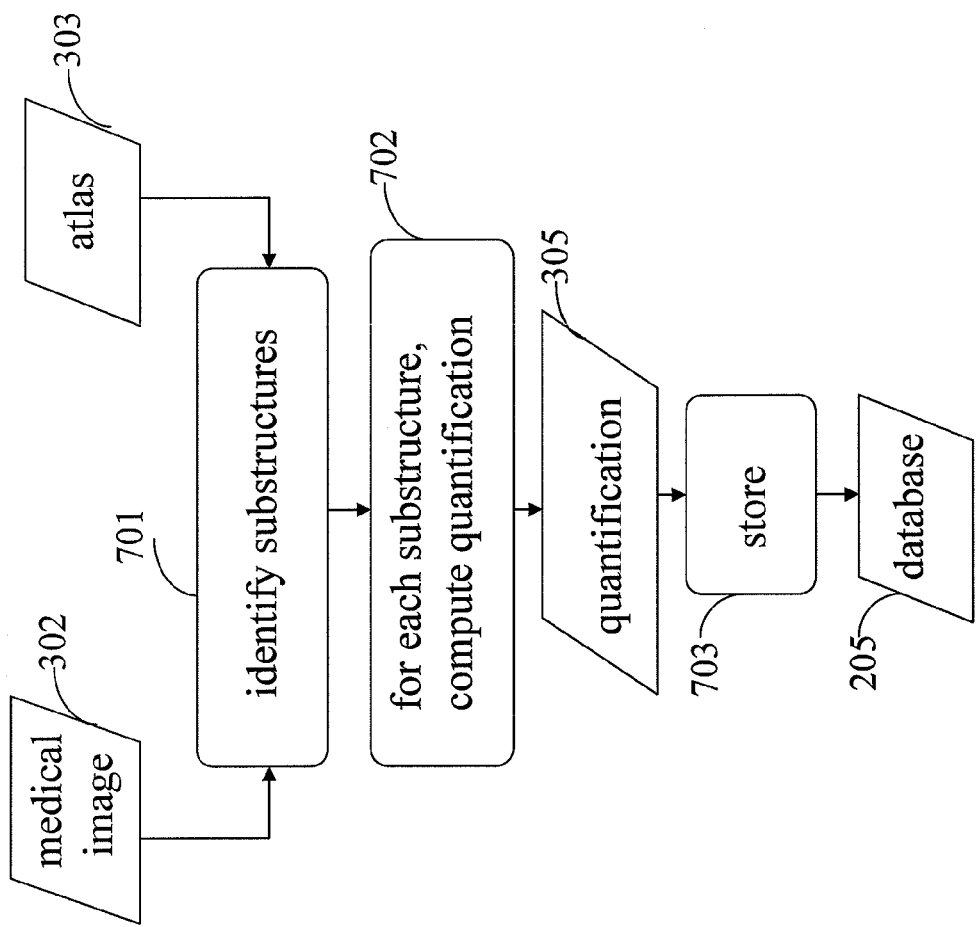
FIG. 7 shows a flow chart according to some embodiments of the current invention.

To build up database 205, additional images may be incorporated. FIG. 7 shows a flow chart illustrating processes, implemented by one or more processors executing software code stored on one or more data storage devices, according to some embodiments of the present invention. The processors may be signal processors, computer processors, or combinations thereof. Example signal processors may include programmed field programmable gated array (FPGA) chips, programmed digital signal processing (DSP) chips, application specific integrated circuits (ASIC) chips, etc. Example computer processors may include single core or multi-core central processing units (CPU), single-core or multi-core graphic unit processing (GPU) chips, etc. In some embodiments of the current invention, the processes illustrated in FIG. 2A can be performed by data storage unit 102 and signal process unit 103.

In block 701, an input medical image 302 representing a tissue region of a subject may be received from a first data storage device. The medical image may include a plurality of image voxels. Input medical image 302 may include a 3-D image. Meanwhile, an atlas 303 of said tissue region may be received, from the first data storage device or a second data storage device. The atlas may comprise spatial information of at least one substructure in the tissue region. Thereafter, a portion of image voxels corresponding to each of the at least one substructure of said tissue region may be identified on input medical image 302. The identification may utilize the spatial information of the at least one substructure in the atlas 303.

In block 702, a computed quantification 305 of the portion of image voxels corresponding to each of the at least one substructure of said tissue region may be provided by performing spatial filtering on the input medical image based on the portion of image voxels for the corresponding substructure. Computed quantification 305 may include one of a volume, an area, a sum, a mean, a median, a standard deviation, a standard error, etc.

In block 703, the information encoding computed quantification 305 may be stored into database 205. The storing may be an appending operation that stores the information encoding computed quantification 305 as a tag to the corresponding image. The information may be expressed in a scalar, vector, a matrix, etc.

Figure 8:
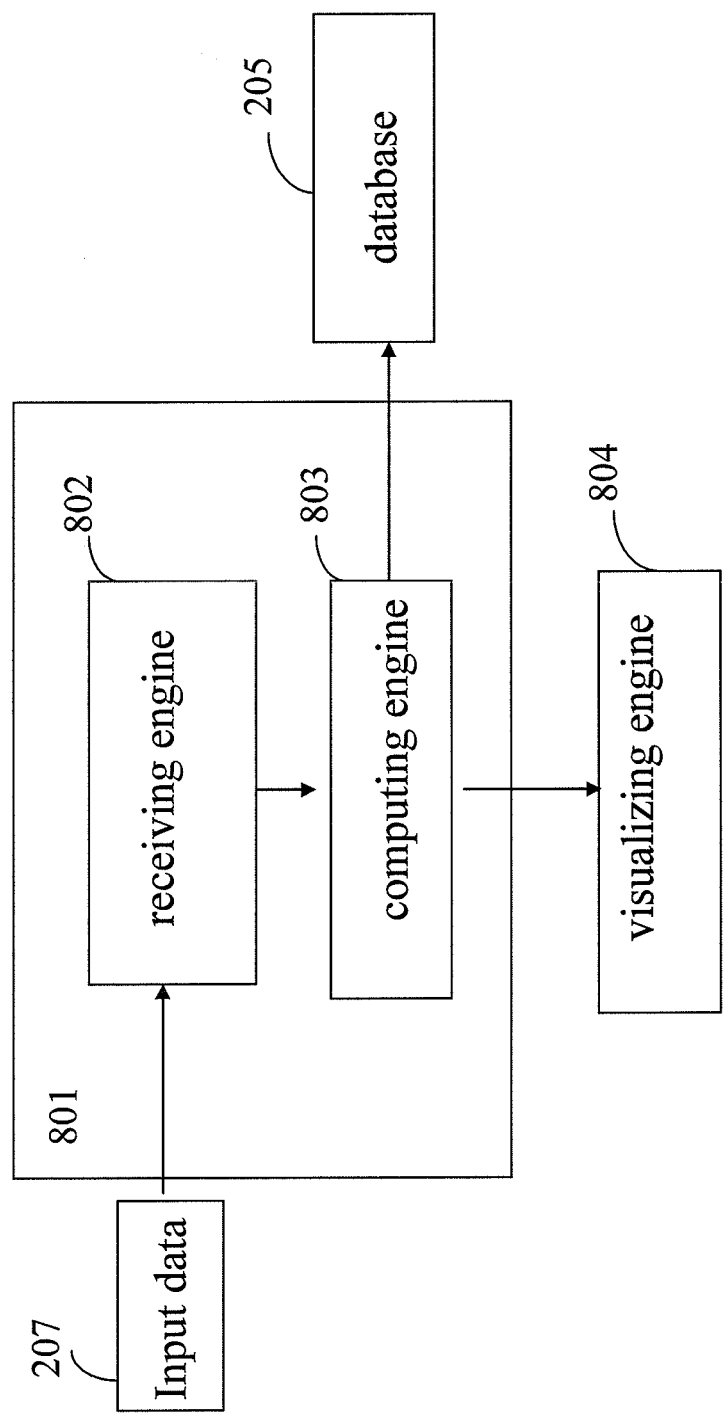
FIG. 8 shows the schematics of another workstation according to another embodiment of the current invention.

FIG. 8 shows a workstation 801 according to some embodiments of the current invention. The workstation may include a receiving engine 802 and a computing engine 803.

Receiving engine 802 may be adapted to receive a medical image representing a tissue region from a subject, the medical image may be a 3-D digital image and include a plurality of image voxels. The subject may be a human patient, an animal, or a sample. Receiving engine 802 may also receive an atlas of said tissue region, the atlas may include spatial information of at least one substructure in the tissue region.

Computing engine 803 may be adapted to identify, for each of the at least one substructure in the tissue region, a corresponding portion of image voxels in the medical image based on the spatial information of the at least one substructure in the atlas; and provide a computed quantification of the corresponding portion for each of the at least one substructure by performing spatial filtering on the medical image. Computing engine 803 may be further adapted to store the information encoding the computed quantification to database 205. The information encoding the computed quantification may be stored along side the corresponding medical image in the database 205. Database 205 may reside on data storage device 102 as discussed above.

Workstation 801 may further include a visualizing engine 804 to display one of the medical image or the quantification from the computing engine 803. Visualizing engine 804 may be, for example, a display device or a printing device. Example display devices may include, for example, a cathode ray tube (CRT), a light-emitting diode (LED) display, a liquid crystal display (LCD), a digital light projection (DLP) monitor, a vacuum florescent display (VFDs), a surface-conduction electron-emitter display (SED), a field emission display (FEDs), a liquid crystal on silicon (LCOS) display, etc. Example printing devices may include, for example, toner-based printers, liquid ink-jet printers, solid ink printers, dye-sublimation printers, and inkless printers such as thermal printers and ultraviolet (UV) printers, etc. However, display and printing devices are not limited to these particular examples. They can include other existing or future developed devices without departing from the scope of the current invention.

Workstations 201 and 801 may be a computer with at least one central processing unit (CPU) and a plurality of memories. Workstations 201 and 801 may also be a dedicated processing machine with such devices as, for example, a field programmable gated array (FPGA), a digital signal processing (DSP) chip, a graphic processing unit (GPU), an application specific integrated circuit (ASIC), etc. Workstations 201 and 801 may also be incorporated in the imaging system 100.

The engines may be implemented by a computer with at least one processor and a plurality of memories. The processor may be, for example, one or more single-core or multi-core central processing unit (CPU), one or more single-core or multi-core graphic processing unit (GPU), etc. The computer may be a distributed computer comprising more than one processor connected via a network to divide the computation. Example networks may include, but is not limited to, an intranet, an extranet, the internet, or combinations thereof. Receiving engines 202 and 802, computing engines 203 and 803 may be implemented by, for example, a field programmable gated array (FPGA), a digital signal processing (DSP) chip, a graphic processing unit (GPU), an application specific integrated circuit (ASIC), etc.

Picture Archiving and Communication System (PACS) is an image-based database widely used in daily radiological diagnosis. The images are searchable based on patient information, which can be retrieved and viewed in off-line stations. Integration (or linkage) of clinical records and diagnosis information to PACS systems is one of the research areas under active development, which is expected to enable clinicians to search past cases based on patients' clinical status. While the electronic medical recording systems are under constant evolution, there is one significant yet missing technology to fully utilize the content of PACS systems; namely a technology to search stored images based on image feature such as the anatomical substructures. Without this technology, images and metadata of past cases stored in PACS are rarely used to enrich current diagnosis efforts.

The technology to search and retrieve images based on their features is called content-based image retrieval (CBIR), a highly active research field for computer vision and image processing, such as face recognition (Muller, Michoux et al. 2004). This is also a highly anticipated technology in medical imaging for CT (Robinson, Tagare et al. 1996; Greenspan and Pinhas 2007; Rahman, Bhattacharya et al. 2007) and MRI (Orphanoudakis, Chronaki et al. 1996; El-Kwae, Xu et al. 2000; Sinha, Ton et al. 2001; Muller, Rosset et al. 2005; Unay, Ekin et al. 2010). If the stored images are available for direct search and retrieval, one could search past cases that share similar anatomical features with the new patient of interest. The implication is far-reaching. For example, if one can retrieve past 100 images with a similar brain atrophy pattern with a dementia patient, the associated metadata summary can be generated such as probability of diagnosis and prognosis (e.g., the 5-year functional outcome of the age-matched past patients). This capability could greatly enhance decision-making confidence in the diagnosis of new cases. This capability can also provide a new platform for advanced anatomy-functional correlation research by rendering a vast clinical database available for searching, thereby greatly benefiting, for example, medical teaching and education.

While the CBIR is certainly a much sought-after technology, to date, very few visual image retrieval system have been used in routine clinical practice as well as educational resources (Muller, Michoux et al. 2004). One of the enabling technologies for CBIR may include the ability to automatically extract the anatomical features and convert them to an entity that is readily searchable such as a scalar, a vector, or a matrix. In general, gray scale, color, texture or shape may be used for the feature extraction (Kassner and Thornhill 2010). One of the difficulties to apply these established CBIR to the human brain is the complexity of the structures and the importance of location information. For example, atrophy in the caudate has totally different prognosis implications from atrophy in the hippocampus. This complexity means that it is essential to establish a consistent coordinate system to define equivalent brain locations across patients. The most widely used approach for this purpose is the voxel-based analysis, in which each patient brain is transformed to a standard coordinate system such as the MNI/ICBM coordinates and each location is referred by x, y, z coordinates (Ashburner and Friston 2000). This approach, however, presents a computational challenge with an overwhelming amount of location information (e.g., at 1 mm image resolution, there would be about 1 million pixels). Confounding the computational challenge is the fact that the information from each pixel could be highly noisy. Accordingly, automatic segmentation of the input image into a small number of structural units may be beneficial. For automated segmentation of brain structures, intensity-based tissue classification and label propagation methods have been postulated (Iosifescu, Shenton et al. 1997; Fischl, Salat et al. 2002; Hammers, Allom et al. 2003; Fischl, van der Kouwe et al. 2004; Rohlfing, Russakoff et al. 2004; Smith, Jenkinson et al. 2004; Svarer, Madsen et al. 2005; Heckemann, Hajnal et al. 2006; Yushkevich, Piven et al. 2006). To apply the computer-assisted brain segmentation for anatomic feature extraction, image searching, and clinical diagnosis support, the segmentation procedure needs to be fully automated and the entire brain needs to be characterized. To date, there are no reports describing anatomical labeling of the full brain, effectiveness of feature extraction, and accuracy of retrieving past similar cases.

In this application, an image search and retrieval tool has been proposed. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A non-invasive imaging system, comprising:
   an imaging scanner suitable to generate an image representing a tissue region of a subject under observation, the tissue region having at least one substructure and said image comprising a plurality of image voxels;
   a signal processing system in communication with said imaging scanner to receive the image from said imaging scanner; and
   a data storage unit in communication with said signal processing system,
   wherein said data storage unit is configured to store:
   an atlas comprising spatial information of said at least one substructure in the tissue region, and
   a database comprising a plurality of pre-stored medical images representing said tissue region, and
   wherein said signal processing system is adapted to:
   segment said image, for each of the at least one substructure, into a corresponding portion of image voxels in said image using the atlas;
   store a computed quantification of the corresponding portion of image voxels for each of the at least one substructure of said tissue region in said database, said computed quantification being calculated by performing spatial filtering on said image, said spatial filtering including said segmenting; and
   search said database using a computed quantification value as input to provide at least one selected medical image from the plurality of pre-stored medical images, the at least one selected medical image having a corresponding quantification that is substantially similar to said computed quantification value.

2. The non-invasive imaging system according to claim 1, wherein said imaging scanner comprises one of: a magnetic resonance imaging (MRI) scanner, a computed tomography (CT) imaging scanner, a positron emission tomography (PET) imaging scanner, a single positron emission computed tomography (SPECT) imaging scanner, a ultrasound scanner, or a microscopy scanner.

3. The non-invasive imaging system according to claim 1, wherein said database complies with a Digital Imaging and Communications in Medicine (DICOM) standard.

4. The non-invasive imaging system according to claim 1, wherein said database is integrated into a Picture Archiving and Communication System (PACS).

5. The imaging system according to claim 1, further comprising:
   a viewing station or a console station configured to display at least one of: the image representing said tissue region, or the at least one selected medical image from the plurality of pre-stored medical images in said database.

6. A workstation, comprising:
   a receiving engine adapted to:
   receive an input medical image representing a tissue region from a subject, said input medical image comprising a plurality of image voxels;
   receive an atlas of said tissue region, said atlas comprising spatial information of at least one substructure in the tissue region; and
   receive a database comprising a plurality of pre-stored medical images representing said tissue region on a data storage device;
   a computing engine adapted to:
   segment said input medical image, for each of the at least one substructure in said tissue region, into a corresponding portion of image voxels in the input medical image by using said spatial information from said atlas; and
   store, for each of the at least one substructure in said tissue region, a computed quantification of the corresponding portion of image voxels in said database, said computed quantification being calculated by performing spatial filtering on said input medical image, said spatial filtering including said segmenting; and
   a search engine adapted to search said database using a computed quantification value as input to select at least one of the plurality of pre-stored medical images with a corresponding quantification that is substantially similar to said computed quantification value.

7. A workstation of claim 6, wherein said data storage device is one of a hard disk drive (HDD), a network area storage (NAS) device, a redundant array of independent disks (RAID), a flash drive, an optical disk, a magnetic tape, a magneto-optical disk, or equivalents thereof.

8. A workstation of claim 6, further comprising a visualization engine adapted to display the at least one of the selected medical images.

9. A workstation of claim 6, wherein said search engine is further adapted to provide a statistical report for said subject, said statistic report is based on said search and comprises at least one of: a diagnosis, a prognosis, or functional status.

10. A non-transitory computer readable medium comprising software instructions, which instructions when executed by a computer, causes the computer to:
    receive, from a first data storage device, an input medical image representing a tissue region from a subject, said input medical image comprising a plurality of image voxels;
    receive, from the first data storage device or a second data storage device, an atlas of said tissue region, said atlas comprising spatial information of at least one substructure in the tissue region;
    receive, from the first data storage device or the second data storage device or a third data storage device, a medical image database comprising a plurality of pre-stored medical images;
    segment said input medical image, for each of the at least one substructure of said tissue region, into a corresponding portion of image voxels in the input medical image by using the spatial information in said atlas;

store, for each of the at least one substructure of said tissue region, a computed quantification of the corresponding portion of image voxels in said database, said computed quantification being calculated, said computed quantification being calculated by performing spatial filtering on said input medical image, said spatial filtering including said segmenting; and search said database using a computed quantification value as input to select at least one of the plurality of pre-stored medical images having a corresponding quantification that is substantially similar to said computed quantification value.

11. A non-transitory computer readable medium according to claim 10, wherein said search comprises at least one correlation analysis.

12. A non-transitory computer readable medium according to claim 11, wherein said correlation analysis comprises one of: a principal component analysis, a maximum likelihood analysis, a least mean square analysis, or a student t-test.

13. A non-transitory computer readable medium according to claim 12, wherein said input medical image comprises a 3-D image.

14. A computer-implemented method to construct a medical image database, the method comprising:

receiving, from a first data storage device, a medical image representing a tissue region of a subject, said medical image comprising a plurality of image voxels;

receiving, from the first or a second data storage device, an atlas of said tissue region, said atlas comprising spatial information of at least one substructure of said tissue region;

segmenting the medical image into image voxels corresponding to each of the at least one substructure of said tissue region using said atlas;

performing spatial filtering on said medical image based on the image voxels identified for each of the at least one substructure to provide a computed quantification thereof, said spatial filtering including said segmenting; and storing, in said database, information encoding said computed quantification for each of said at least one substructure identified on the medical image in said database, said database residing on the first or the second data storage device or a third data storage device, wherein said database is configured to be searched using a computed quantification value that is operable to retrieve a medical image that corresponds to said computed quantification value.

15. A method according to claim 14, wherein said medical image is a 3-dimensional (3-D) image.

16. A method according to claim 14, wherein said medical image is one of a computed tomography (CT), a magnetic resonance imaging (MRI) image, a positron emission tomography (PET) image, a single positron emission computed tomography (SPECT) image, an ultrasound (US) image, an optical coherence tomography (OCT) image, or a microscopy image.

17. A method according to claim 14, wherein said tissue region is on of: a brain, a liver, a heart, a kidney, a breast, a joint, or a vessel.

18. A method according to claim 14, wherein said substructure is one of an anatomic substructure or a physiologic substructure.

19. A method according to claim 14, wherein said identifying uses at least one elastic transform.

20. A method according to claim 19, wherein said elastic transform comprises a diffeomorphic transformation.

21. A method according to claim 14, wherein said computed quantification comprises one of:

a volume, an area, a sum, a mean, a median, a standard deviation, or a standard error.

22. A method according to claim 14, wherein said storing saves information encoding said computed quantification along with said medical image on the same data storage device.

23. A method according to claim 14, wherein said information encoding said computed quantification is stored as a tag to said medical image.

24. A method according to claim 14, wherein said information encoding said computed quantification comprises one of a scalar, a vector, or a matrix.

25. A method according to claim 14, wherein said database complies with a Digital Imaging and Communications in Medicine (DICOM) standard and comprises said information encoding said computed quantification.

26. A method according to claim 25, wherein said database is integrated into a Picture Archiving and Communication System (PACS).

27. A workstation, comprising:

a receiving engine adapted to:

receive a medical image representing a tissue region from a subject, said medical image comprising a plurality of image voxels; and receive an atlas of said tissue region, said atlas comprising spatial information encoding at least one substructure of said tissue region; and a computing engine adapted to:

segment said medical image, according to spatial information in said atlas, into image voxels that correspond to each of the at least one substructure of said tissue region;

perform spatial filtering on said medical image based on the image voxels identified for each of the at least one substructure to provide a computed quantification thereof, said spatial filtering including said segmenting; and store, on a non-transitory data storage device, information encoding said computed quantification of each of said at least one substructure identified on the medical image, wherein said information provides an addition to a database of medical images residing on said non-transitory data storage device, and wherein said database is configured to be searched using a computed quantification value that is operable to retrieve a medical image that corresponds to said computed quantification value.

28. A workstation of claim 27, wherein said non-transitory data storage device is one of a hard disk drive (HDD), a network area storage (NAS) device, a redundant array of independent disks (RAID), a flash drive, an optical disk, a magnetic tape, a magneto-optical disk, or equivalents thereof.

29. A workstation of claim 27, further comprising a visualization engine adapted to display one of: image voxels from the medical image identified as corresponding to one of the at least one substructure of said tissue region, or information encoding said computed quantification.

\* \* \* \* \*